United States Patent [19]

Idaszak et al.

[11] 3,956,065

[45] May 11, 1976

[54] INERT, NON-POROUS GRANULES FOR FLOW CONTROL IN A PLUG FLOW REACTOR

[75] Inventors: Leo R. Idaszak, Palos Heights; Richard A. Terranova, Argo; Robert E. Heady, Park Forest, all of Ill.

[73] Assignee: CPC International Inc., Englewood Cliffs, N.J.

[22] Filed: Feb. 2, 1973

[21] Appl. No.: 328,996

[52] U.S. Cl. .............................. 195/31 F; 195/115; 195/116
[51] Int. Cl.² ...................................... C12D 13/00
[58] Field of Search ............. 195/31 F, 68, 63, 115, 195/31 R, 116; 55/91; 261/94, 98

[56] References Cited
UNITED STATES PATENTS

| | | | |
|---|---|---|---|
| 3,251,749 | 5/1966 | Lipps | 195/115 |
| 3,282,702 | 11/1966 | Schreiner et al. | 195/63 X |
| 3,364,656 | 1/1968 | Whiton et al. | 55/91 |
| 3,409,279 | 11/1968 | Metrailer | 261/94 |
| 3,432,994 | 3/1969 | Whiton et al. | 55/91 |
| 3,652,761 | 3/1972 | Weetall et al. | 195/68 X |
| 3,753,858 | 8/1973 | Takasaki et al. | 195/31 F |
| 3,775,254 | 11/1973 | Buetow | 195/68 X |
| 3,783,101 | 1/1974 | Tomb et al. | 195/63 |
| 3,788,945 | 1/1974 | Thompson et al. | 195/63 X |
| 3,796,657 | 3/1974 | Pretorius et al. | 261/94 |
| 3,847,741 | 11/1974 | Heady | 195/31 F |

*Primary Examiner*—A. Louis Monacell
*Assistant Examiner*—Thomas G. Wiseman
*Attorney, Agent, or Firm*—Donald George Marion

[57] ABSTRACT

Process of enzymatically converting glucose to fructose wherein a glucose-containing solution is passed, under specific conditions, through a bed composed of an immobilized glucose isomerase in a fine, particulate form and non-porous beads or granular inert material such as polystyrene beads. The porous beads and granular inert material comprise between 40% and about 75% of the bed by volume. The bead's presence exerts a buoyant effect which prevents bed packing and promotes desirable flow patterns with no observable channelling. This helps to minimize the formation of undesired or undesirable carbohydrates such as psicose.

13 Claims, 1 Drawing Figure

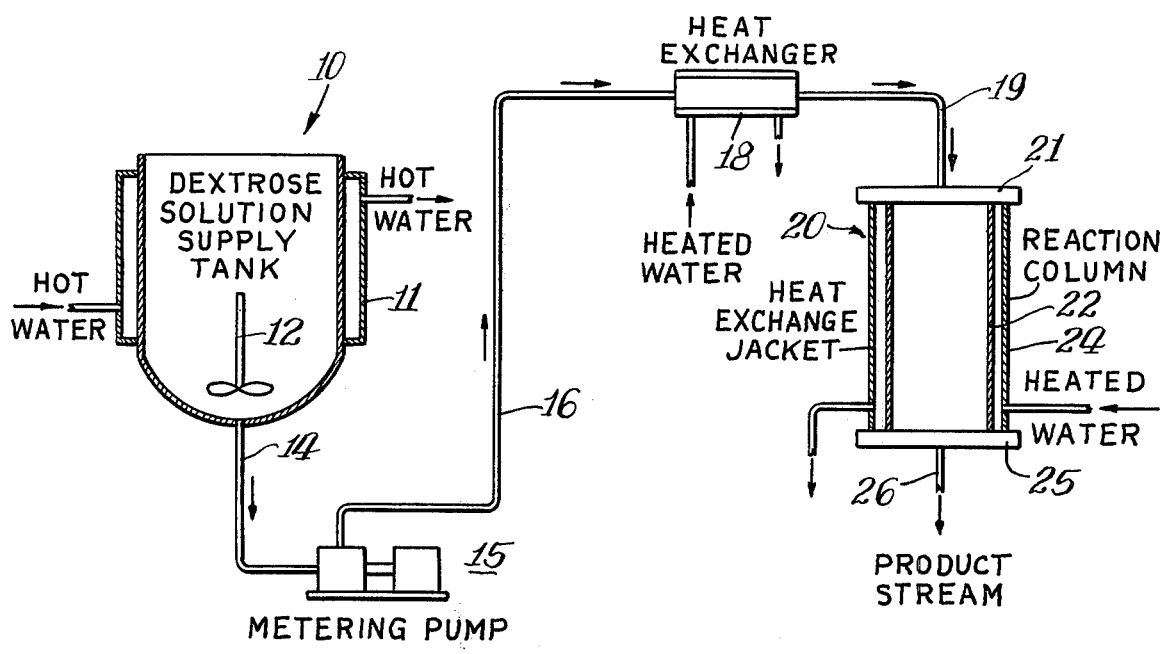

INERT, NON-POROUS GRANULES FOR FLOW CONTROL IN A PLUG FLOW REACTOR

INTRODUCTION

This application relates to improved technology for conducting enzymatic reactions. More specifically, the invention relates to improved technology for the enzymatic isomerization of dextrose to levulose.

PRIOR ART

Since Marshall and Kooi first published information about the enzymatic isomerization of dextrose to levulose in *Science*, Apr. 5, 1957, Vol. 125, pages 648–649, many attempts have been made to develop commercially attractive enzymatic isomerization processes.

From experimental work with enzymatic isomerization, primarily with batch processes, some familiarity has developed with the parameters of the isomerization process. It appears that, for a continuous isomerization utilizing intact cells as the source of isomerizing activity, a pH of about 7–8 is desirable for cell integrity.

In view of the effect of alkaline ph on sugar degradation, it is desirable to utilize as short an isomerization time as possible, to minimize sugar degradation, and also to minimize the formation of organic acids that inherently occurs during enzymatic isomerization.

It has long been recognized that immobilized enzymes represent an attractive physical form about which continuous enzymatic processes can be designed. once an enzyme has been placed in a suitable immobilized form, processes utilizing the enzyme can be practiced by passing a solution of the substrate to be converted through a column of the immobilized enzyme. The rate and degree of conversion is a function of the parameters of the column and of the rate of flow through the column. Early examples of immobilized enzyme column reactions can be found in U.S. Pat. No. 3,165,485, granted Jan. 26, 1965.

One of the earliest attempts to carry out a continuous isomerization in a column is described, in the Japanese language, in the *Japanese Journal of Food Science and Technology* (Nippon Shokuhin Kogei Gakkaishi), Vol. 14, pages 539–540 (1967), "Continuous Isomerization of Glucose by a Column of Glucose Isomerase". In this article, the authors Tsumura and Ishikawa described the immobilization of an isomerizing enzyme from *Streptomyces phaeochromogenes* on DEAE-Sephadex. The immobilized enzyme was disposed in a column that was surrounded by a heat jacket, and a dextrose solution was supplied to the top of the column. Continuous isomerization was carried out at a pH in the range from about 7.6 to about 7.8, and at a jacket temperature of about 60°C. Levulose-bearing solutions were recovered.

Subsequently, Takasaki et al described the use of heat-treated cells of *Streptomyces albus* in a jacketed column for continuous isomerization in the text, *Fermentation Advances*, pages 561–589, Academic Press, 1969 (see particularly pages 569 and 570). More recently, the use of a pressure leaf filter, in conjunction with a bed of heat-treated cells, has been described in U.S. Pat. No. 3,694,314, granted Sept. 26, 1972.

OBJECTS OF THE INVENTION

One object of the present invention is to provide an improved process for conducting enzymatic reactions on a continuous basis.

A more specific object of the invention is to provide a practical process for the continuous isomerization of dextrose to levulose.

A related object of the invention is to provide an improved type of bed for conducting enzymatic reactions in plug flow reactors.

Another object of the invention is to provide an improved bed design for continuously conducting enzymatic reactions in plug flow reactors, and specifically, a bed design that is particularly useful where the enzyme preparation is in the form of cells of the microorganism.

A further object of the invention is to provide a practical enzymatic process for the conversion of dextrose to levulose, in which the formation of undesired and/or undesirable carbohydrates is minimized.

Other objects of the invention will appear hereafter from the specification and from the recitals of the appended claims.

DEFINITIONS

Because of the many terms that are in common use in the art, a few definitions are made to simplify the present application and permit it to be more concise.

*D.E.:* The term "D.E." is an abbreviation for "dextrose equivalent," and these terms are used interchangeably to refer to the reducing sugar content of a material calculated as dextrose and expressed as percent of total solids.

*Starch Hydrolysate:* The term "starch hydrolysate" is used in a general way to refer to a syrup or dry product that is made by the hydrolysis of starch. Such a product may be made by acid or enzymatic hydrolysis, or by a combination of acid and enzymatic hydrolysis. A preferred type of starch hydrolysate for use for isomerization in accordance with the present invention is produced by acid or enzyme thinning to a D.E. of 10 or less, followed by enzymatic saccharification to a D.E. above 95, and preferably above 97.5.

*Glucose and Dextrose:* Medium D.E. starch hydrolysates are commonly referred to in the art as "glucose", whether the starch hydrolysate is in the form of a syrup or in the form of solids. The term "dextrose" is commonly reserved for the refined crystalline monosaccharide that is recovered from a high D.E. starch hydrolysate, or for D-glucose as a constituent of starch hydrolysates. As used hereafter, the term "dextrose" will be used to embrace this monosaccharide in any form, in solution or dry, as a constituent of a starch hydrolysate syrup, syrup solids, or in refined crystalline form.

Fructose and Levulose: The terms "fructose" and "levulose" are generally employed interchangeably in the art to refer to a particular isomer of dextrose that is sweeter than dextrose. This isomer is found in honey and in invert sugar, along with dextrose, and it is valuable because of its sweetness. The term "levulose" will be used to refer to this monosaccharide.

*The Enzyme:* The enzyme that isomerizes dextrose to levulose has been referred to in the art by several names. It is referred to in the Marshall U.S. Pat. No. 2,950,228, as xylose isomerase, because it isomerizes xylose to xylulose. This activity is in addition to its ability to isomerize dextrose to levulose. It has also been referred to in the art as dextrose isomerase and glucose isomerase. The term "dextrose isomerase" will be used herein.

*Enzyme Preparation:* The term "enzyme preparation" is used to refer to any composition of matter that exhibits the desired dextrose isomerase enzymatic activity. The term is used to refer, for example, to live whole cells, dried cells, and to refined, concentrated, and immobilized enzyme preparations derived from cells. Since this invention is concerned with continuous processes, the enzyme will always be present in some immobilized form. For example, the enzyme may be immobilized because it is present inside intact cells, or it may be bound to an insoluble matrix. The common methods for binding enzymes to matrices are (1) by adsorption at a solid support surface, (2) by inclusion of the enzyme by entrapment within the matrix of a gel lattice or other polymer having pores large enough to allow the molecules of the substrate and of the product to pass freely, but small enough to retain the enzyme, (3) by cross-linking by means of a bifunctional reagent (often with (1) or (2)), and (4) by several different chemical linkage methods.

*Units;* Units: parts and percentages are by weight, and on as is basis, unless expressly stated to be otherwise.

*Isomerase Unit:* One isomerase unit is defined as the amount of enzyme activity that is required to produce 1 micromole of levulose per minute under the isomerization conditions described hereafter under the heading "Assay of Isomerase Activity".

*Streptomyces:* This term refers to a genous of microorganisms of the order of Actinomycetales. These microorganisms are aerial mycelium-producing actinomycetes. The genus is well recognized. Some of its important distinguishing characteristics are described, for example, in the text "The Actinomycetes," by Selman A. Waksman, The Ronald Press Company, New York, 1967, page 135 et seq.

Assay Of Isomerase Activity

The assay procedure involves making a spectrophotometric determination of the ketose produced from a glucose solution under a standardized set of conditions.

A stock solution is made up in the following manner:

TABLE 1

Stock Solution for Assay

| Component | Amount |
|---|---|
| 0.1 M MgSO$_4$ 7H$_2$O | 1 ml. |
| 0.01 M CoCl$_2$ 6H$_2$O | 1 ml. |
| 1 M phosphate buffer, pH 7.5 | 0.5 ml. |
| Anhydrous D-glucose | 1.44 grams |
| Distilled water | To make up a total volume of 7.5 ml. |

The enzyme preparation to be assayed is first diluted to contain from 1 to 6 isomerase units per ml.

An enzymatic isomerization is conducted by adding 1 ml. of the enzyme preparation to 3 ml. of the stock solution, and incubating for 30 minutes at 60°C. At the end of the incubation period, a 1 ml. aliquot is taken and quenched in a 9 ml. volume of 0.5 N perchloric acid. The quenched aliquot is then diluted to a total volume of 250 ml. As a control, for comparative purposes, a glucose blank is also run by substituting 1 ml. of water for the 1 ml. of the enzyme preparation in solution form, at the beginning of the incubation period.

The ketose is then determined by a cysteine-sulfuric acid method. For the purposes of this assay, one isomerase unit is defined as the amount of enzyme activity that is required to produce one micromole of levulose per minute under the isomerization conditions described.

BRIEF DESCRIPTION OF THE DRAWING

The single FIGURE of drawing is a schematic diagram showing one way in which equipment can be arranged to practice the process of the present invention.

BRIEF SUMMARY OF THE INVENTION

In one preferred mode for practicing the invention, the process involves passing a stream of a solution containing dextrose through a bed that is made up of a substantially uniform mixture of an immobilized enzyme preparation in particulate form, that is characterized by the ability to isomerize dextrose to levulose, and substantially non-porous beads or granules of an inert material. These beads space apart the particles of the enzyme preparation and establish a flow pattern within the bed. In addition, since they are non-porous, the solution that is passing through the bed is not absorbed. The beads therefore reduce the bed volume that is available for occupancy by the dextrose solution or substrate, and minimize substrate residence time in the bed. This in turn minimizes the formation of undesired products, particularly undesired and undesirable carbohydrates such as, for example, psicose.

The temperature that is selected for the isomerization reaction will depend upon the particular enzyme preparation that is used. Different enzyme preparations have different optimum operating temperatures. In addition, the selection of operating temperature will depend upon such considerations as enzyme stability and the formation of by-products. Generally, however, the temperature will be at least 50°C and below about 80°C. A temperature below 50°C can be used, but the reaction rate is undesirably slow. A preferred operating temperature range, particularly for enzymes derived from microorganisms of the Streptomyces genus, is from about 60°C to about 70°C.

The factors that affect the selection of operating pH are analogous to those that affect the selection of operating temperature. Generally, the pH should be kept in the range from about 6.0 to about 9.0. The preferred operating pH is above 7.0, and most preferably, in the range from about 7.5 to about 8.5.

While the inert, non-porous beads may take many forms, the most preferred form comprises polystyrene beads that fall in the range from −18 to +50 U.S. Standard Sieve size. Such beads employed have a lower specific gravity than the substrate or dextrose solution, so that they exert buoyancy within the bed during isomerization. This buoyancy tends to reduce the tendency of the bed to pack and keeps the bed loose, thus promoting a desirable kind of flow pattern within the bed.

The proportions of non-porous, inert beads in the bed will depend upon the kind of enzyme preparation employed and the percentage of other inert materials, such as filter aid, that may be present. Generally, however, for effective results, the beads should form from about 40 to about 75% of the bed by volume.

DETAILED DESCRIPTION OF THE INVENTION

Referring now in detail to the single FIGURE of drawing, the mumeral 10 denotes a storage tank for the dextrose solution supply. This tank 10 is provided with a heat exchange jacket 11 through which hot water can be circulated to maintain the supply solution at an elevated temperature. The tank is also provided with an impeller 12 (shown schematically, without any power source) to keep the solution mixed and at a substantially uniform concentration.

The tank 10 is connected through a line 14 to a metering pump 15, that can transfer the supply solution through a line 16 to a heat exchanger 18. The heat exchanger 18 discharges through a line 19 to the upper end of a reaction column 20.

The reaction column 20 is generally cylindrical and is provided with: a cover plate 21 that can be bolted to the generally cyliindrical side wall 22; a heating jacket 24 about its side wall 22; and a bottom plate 25. The product stream discharges through a line 26 at the lower end of the reaction column.

The present invention is concerned with the material that forms the bed within the column 20.

The inert, non-porous beads, for use in the bed, may have a variety of shapes. For convenience, however, spherical beads are preferred, with a size range from about 0.1 mm. to about 10 mm. in diameter, or preferably, from about 0.3 mm. to about 1.0 mm. (which corresponds to −18 − +50 mesh U.S. Standard Sieve size).

For one preferred mode of operation, the syrup substrate has a specific gravity of about 1.15. Spherical glass beads have a bulk specific gravity of about 1.5, whereas the corresponding figure for spherical polystyrene beads is about 1.0. The polystyrene beads are preferred because of their apparent buoyant effect during operation.

When spherical beads are placed in a bed in a column, with random packing, the interstitial void space amounts to from about 25 to about 40% of the bed volume. The enzyme preparation ideally is disposed in this interstitial void space. It may be placed there in a variety of ways. One convenient way is to flow it into place in the form of a dilute slurry, utilizing applied vacuum and/or applied pressure to achieve any desired compaction to permit appropriate loading in terms of activity units per unit of volume.

The invention is useful in improving flow characteristics (indeed, in making flow possible in many cases) wherever the enzyme preparation, if used alone, would present a packing or channeling problem.

The invention will now be described in detail and further illustrated by several specific demonstrations of its use.

EXAMPLE 1

Continuous Isomerization Utilizing Microbial Cells As The Enzyme Preparation

Cells of *Streptomyces olivochromogenes* were grown in a fermentor. The growth medium contained xylose as an inducing agent, to cause the cells to secrete dextrose isomerase.

The cells were recovered from the mycelium in the form of a filter cake containing 3 grams of filter aid for each gram of cellular material, dry substance basis. The initial activity of the filter cake-enzyme preparation was 287 units per gram.

A mixture was then made of the filter cake, which served as the enzyme preparation, together with generally spherical polystyrene beads having a smooth, non-porous surface and a mesh size of −18 +50, U.S. Standard Sieve. This mixture was then packed into a cylindrical column, using a particular packing technique.

Thus, the enzyme preparation was soaked in water for 2 hours before it was mixed with the polystyrene beads. The mixture was then loaded into the column in small increments. After each increment was added, a vacuum was applied to the lower, discharge end of the column, to remove the water from the mixture and to cause the material in the column to pack down.

When the water had been substantially completely removed from each increment added to the column, the column was covered, the cover was bolted on, and the column was pressurized with nitrogen. This packed down the mixture in the column. Another increment was then added to the column, and this entire procedure was repeated several times until the column was full.

A supply liquor was made up from a solution of crystalline dextrose and water, at 30°C Baume (60°F/60°F) (700 grams of dextrose per liter). A stream of this substrate was passed through the column, and was permitted to flow downwardly through the bed, at an initial flow rate of about 0.66 bed volumes per hour, where a "bed volume" is calculated as the difference between total bed volume and the volume actually occupied by the beads. In other words, the flow rate is expressed in terms of the interstitial volume of the beads, on the assumption that the active bed of enzyme preparation is equivalent in volume to the interstitial volume of the beads. Stated another way, since the beads are inert, actual bead volume, exclusive of void space, is excluded from bed volume as calculated for flow rate purposes. The term "bed volume" is used consistently hereafter with this same meaning.

The column was maintained in operation for a period of 28 days, and the flow rate was gradually reduced to about 0.25 bed volumes per hour during that period of time. The initial flow rate was adjusted so that the effluent product contained 45% ketose dry basis. The column was then operated at a constant flow rate for more than 9 days, during which the effluent contained 44–45% ketose dry basis. Thereafter, the flow rate was periodically decreased to maintain the effluent at a ketose content of about 45%, until the operations were finally stopped after 28 days of continuous operation. The column was operated at a pH of about 8.0, and at a temperature of about 60°C.

Based on gross bed volume, the loading of the column was $6.96 \times 10^5$ units of isomerase per cubic foot. Throughout the isomerization, the pressure drop through the column was in the range from 50–60 psig at 0.5 bed volumes per hour flow rate.

The product content of undesirable carbohydrates appeared to have a direct relationship, among other things, to the residence time in the column. The psicose content of the effluent stream did not exceed 0.5% dry basis, and generally was 0.2–0.3% dry basis.

The polystyrene beads had a density below that of the dextrose solution. They therefore exhibited buoyancy in the bed during isomerization, and kept the bed loose, to establish a good flow pattern with no observable channelling.

By way of contrast, when attempts had been made to operate a column under generally similar conditions, but with the bed made up of the enzyme preparation described above alone, with no inert, non-porous beads, very high pressure drops were required to maintain the bed in operation, channelling developed, and such generally poor flow patterns developed that commercial operations appeared impractical. Moreover, while the presence of the filter aid in the enzyme preparation does appear to provide some benefits in connection with the hydraulic characteristics of a column containing the enzyme preparation alone, the porosity of filter aid particles tends to hold up some of the substrate liquor within the column and is therefore conducive to side reactions.

EXAMPLE 2

Continuous Isomerization Utilizing A Fixed Bed of Microbial Cells with Polystyrene Beads; Light Column Packing For this example, the column packing procedure was modified to omit the application of nitrogen pressure. Instead, the entire bed was built up by adding an increment of the enzyme preparation of Example 1 to a column previously filled with the polystyrene beads, removing the water by the application of vacuum, then adding another increment, and then repeating the procedure until the column had been filled. The net result of following this modified procedure was that the amount of material packed in the column was less than in Example 1.

Upon starting operations, the pressure drop through the column was observed to be only 20 psig. The column was operated for two days at a flow rate of 0.5 bed volumes per hour. The ketose concentration in the effluent was only 30%. The conclusion is that good packing of the bed in the column is essential for efficient continuous isomerization.

EXAMPLE 3

Continuous Isomerization Utilizing A Bed Of Microbial Cells With Glass Beads

For this demonstration of the invention, a jacketed column was used. The jacket was connected to a source of hot water, for controlling column temperature during isomerization.

A strain of a microorganism of the Streptomyces genus, that is recognized as a good dextrose isomerase producer, was grown under submerged, aerobic conditions on a medium containing xylose, to produce intracellular isomerase.

After fermentation, magnesium hydroxide was added to the fermenter broth in the ratio of two parts by weight of magnesium hydroxide for each one part by weight of the cell mass in the broth, dry basis. The slurry thus obtained was filtered, and the filter cake was then dried in an open pan at room temperature. The activity of the dry enzyme preparation thus obtained was 330 units per gram.

This dry enzyme preparation was dispersed in a 50% W/V solution of dextrose. The slurry was then placed in the jacketed column, and as the slurry was added to the column, small glass beads, approximately 3 mm. in diameter, were added simultaneously. The glass beads served as a support and also prevented the enzyme preparation from plugging up the column. In this fashion, approximately 750 units of the enzyme were charged to the column.

A dextrose syrup at 50% W/V concentration was adjusted to a pH in the range from 7.0 to 7.5 by adding magnesium hydroxide. The syrup was sparged with nitrogen, and was then fed to the top of the column under a nitrogen atmosphere. The isomerization product was collected in aliquots of 15 ml., in test tubes. The test tubes each contained about 5 ml. of 0.5 N perchloric acid to inactivate any soluble isomerase that might be present in the product.

The temperature of the column was maintained at about 60°C during an initial phase of operation. The flow rate of dextrose solution through the column was maintained at a substantially uniform rate, and the ketose content of the effluent was 40–50% on a dry solids basis.

The isomerization was conducted in this manner for nine days before a substantial decrease in enzyme activity became apparent, by a dropping off in the ketose value observed in the effluent. During that initial phase of operation, the average ketose content of the effluent was 38.7%.

At the end of this initial phase of operation, the temperature of the column was increased from the initial level of 60°C to 70°C in a single step. Isomerization was then continued, at the increased temperature, for an additional period of 24 hours. The ketose content of the product averaged out at about 49%, for the second phase of operation. The results are summarized below in Table 2.

TABLE 2

Continuous Isomerization: Single Step Temperature Adjustment

| Time Days | Temperature °C | Bed Volume Throughput Per Hour | Output of Approximately 42% d.b. Levulose Product (lbs. d.s. per cu. ft. of bed) |
| --- | --- | --- | --- |
| 1 | 60 | 1.27 | 951 |
| 2 | 60 | 1.27 | 951 |
| 3 | 60 | 1.27 | 951 |
| 4 | 60 | 1.27 | 951 |
| 5 | 60 | 1.25 | 936 |
| 6 | 60 | 1.17 | 876 |
| 7 | 60 | 1.10 | 823 |
| 8 | 60 | 1.03 | 771 |
| 9 | 70 | 1.65 | 1235 |
| 10 | 70 | 1.65 | 1235 |

EXAMPLE 4

Continuous Isomerization Utilizing a Bed of Immobilized Enzyme with Glass Beads

For this demonstration of the invention, a plain glass column was used, and the isomerization was conducted at room temperature.

The column was loaded with a mixture of 754 parts by weight of glass beads and 31.2 parts by weight of the enzyme preparation, which was dextrose isomerase immobilized on DEAE cellulose. In terms of activity, the column loading was 4.8 million units per cubic foot or 2,983 units per gram.

The substrate was prepared by adding to a 12.4° Baume dextrose solution a sufficient quantity of magnesium hydroxide to adjust the pH to 7.8. The feed solution was then passed through the column, to effect isomerization. Observations were made with the feed passing through the column under gravity, and under several different applied pressures. A substantially linear relationship was observed between flow rate and pressure drop through the column, where the flow rate was calculated in bed volumes per hour.

The use of a pressure drop through the column is advantageous since it permits a higher throughput rate for a given piece of equipment. Flow rates from about one bed volume per hour under gravity, to 5 bed volumes per hour under 5 psi gauge, up to as high as 40 bed volumes per hour under a pressure drop of 40 psi gauge, were successfully used with this particular piece of equipment. Since the substrate is a rather viscous solution, and its viscosity decreases as its temperature is increased, even high flow rates can be obtained.

Similarly favorable flow rates were observed when the column was packed with a mixture of an enzyme preparation of dextrose isomerase immobilized on DEAE starch and beads.

Generally speaking, less favorable results are obtained when the column is packed with the enzyme preparation alone, such as, for example, dextrose isomerase that is immobilized on DEAE cellulose, or dextrose isomerase that is immobilized on DEAE starch, as compared to operations when the column is packed with a mixture of the enzyme preparation with beads. In columns packed with enzyme preparations of this type, the polystyrene beads seem to be preferable to glass beads under similar operating conditions, since the flow rates are generally better with beds utilizing the polystyrene beads.

The improvement that is obtained in the flow rate is very responsive to the proportion of beads present. Thus, when the enzyme preparation that is employed in the column is dextrose isomerase that is immobilized on DEAE cellulose, a substantial improvement in flow rate can be obtained when the proportion of beads is adjusted so that the volume of the enzyme preparation in the bed is approximately equal to the interstitial void volume of the beads as distributed in normal, random packing (that is, an interstitial void volume of about 41%), as compared to lower amounts of beads.

GENERAL

The use of inert, non-porous beads in an isomerization bed is advantageous whenever the enzyme preparation, if used alone, tends to pack into a hard bed and require a high pressure drop, for passage through the column at a reasonable flow rate. Any enzyme preparation that is characterized by the presence of a large number of fine particles would fall into this category. Also, any enzyme preparation that tended to form a compressible cake would have its flow performance substantially improved by the use of beads in accordance with the present invention.

In the foregoing specific examples, the enzymes were derived from microorganisms of the Streptomyces genus. However, the present invention can be practiced with dextrose isomerase that is derived from any microorganism, and as is demonstrated in some of the examples, the dextrose isomerase activity in the column can actually be derived from the cells themselves as packed into the column. Similarly, the enzyme activity may be present in the form of a dextrose isomerase that has been recovered in purified form and immobilized on a carrier by any of the immobilization techniques that preserve enzyme activity.

For example, to produce a stabilized dextrose isomerase, a high purity enzyme is recovered from a microorganism source. A Streptomyces-derived enzyme is generally preferred at present, but the source microorganism may be any satisfactory enzyme producer. The high purity enzyme is placed in solution, and the solution is then passed over a bed of finely divided, particulate basic magnesium carbonate. The enzyme is efficiently adsorbed, and the product is a very stable, active form of the enzyme. Other adsorbents can also be used to produce adsorbed immobilized enzymes. For example, a high purity enzyme in solution can also be absorbed on activated charcoal granules or on any other suitable, particulate, solid adsorbent, for use as the enzyme preparation in preparing a bed for a plug reactor in accordance with the present invention.

There are several important advantages that accrue from the practice of the present invention. As compared to batch isomerization, the same amount of enzyme activity, when utilized in accordance with the present invention, produces more levulose product than batch processing. Up to three times more levulose product has been produced from a given amount of enzyme preparation, by practicing the present invention, than is obtained when optimum processing batch techniques are employed.

In addition, there are many other important advantages. When a column is employed in accordance with prior art teachings, difficulties are encountered in avoiding high pressure drops across the column, and whenever a high pressure drop develops, channelling usually occurs. Channelling, of course, produces poor substrate-enzyme contact, makes the operation inefficient, and permits a high residence time for the substrate liquid that is passing through the bed outside of the channels. When the commercially available filter aids which are in the form of pourous particles, are incorporated in a column for the purpose of reducing the pressure drop, the concommitant result is that there is an extended residence time in the column, and consequent undesirable by-product formation. The use of the present invention reduces pressure drop and eliminates channelling without increasing residence time.

Moreover, the very brief residence times that obtain when the present invention is practiced subject the sugar to low thermal hazard. For this reason, the finished product contains few color bodies, so that product color is superior and refining costs are lower. In addition, fewer organic acids are formed, and the carbohydrate composition of the end product is more desirable. Also, because of the shorter processing time, smaller inventories are required.

When the invention has been described in connection with specific embodiments thereof, it will be understood that it is capable of further modifications, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention.

What is claimed is:

1. A process for the enzymatic isomerization of dextrose to levulose that comprises passing a solution containing dextrose through a bed comprising:
   a. a particulate enzyme preparation that is characterized by the ability to isomerize dextrose to levulose; and
   b. substantially inert, non-porous beads having a lower specific gravity than the solution containing dextrose, distributed substantially uniformly in the bed, to space apart the particles of the enzyme preparation and exert a buoyant action and to establish the flow pattern in the bed.

2. A process in accordance with claim 1, wherein the particulate enzyme preparation comprises cells of a Streptomyces microorganism.

3. A process in accordance with claim 1 wherein the enzyme preparation comprises a dextrose isomerase that is immobilized on a particulate inorganic material.

4. A process in accordance with claim 1 wherein the enzyme preparation comprises a dextrose isomerase that is adsorbed on particles of basic magnesium carbonate.

5. A process in accordance with claim 1, wherein the beads are polystyrene beads.

6. A process for the enzymatic isomerization of dextrose to levulose that comprises passing a solution containing dextrose at a pH in the range of from about 6 to about 9, and at a temperature in the range from about 20°C to about 80°C through a bed in a confined reaction zone comprising:
   a. a particulate enzyme preparation that is characterized by the ability to isomerize dextrose to levulose; and
   b. substantially inert, non-porous beads having a lower specific gravity than the solution containing dextrose, distributed substantially uniformly in the bed to space apart the particles of the enzyme preparation and exert a buoyant action and to establish the flow pattern in the bed.

7. A process in accordance with claim 6, wherein the beads are polystyrene beads.

8. A process in accordance with claim 6 wherein the enzyme preparation comprises a dextrose isomerase that is immobilized on DEAE cellulose.

9. A process in accordance with claim 6 comprising forming the bed with beads that form from about 40 to about 75% of the bed by volume.

10. A process in accordance with claim 9 wherein the enzyme preparation comprises cells of a Streptomyces microorganism.

11. A process in accordance with claim 9 wherein the enzyme preparation comprises a dextrose isomerase that is immobilized on a particulate inorganic carrier material.

12. A process in accordance with claim 9 comprising maintaining a superatmospheric pressure drop through the bed.

13. A process for the enzymatic isomerization of dextrose to levulose comprising the steps of;
   a. passing a solution containing dextrose at a pH in the range of about 6 to about 9, and a temperature in the range of about 50°C to about 80°C, through a bed in a confined reaction zone, said bed comprising:
      i. a dextrose isomerase that is immobilized on DEAE cellulose, and
      ii. non-porous polystyrene beads that have a lower specific gravity than said solution containing dextrose, said beads being generally spherical and having a mesh size in the range −18 +50, U.S. Standard Sieve, to space apart the immobilized dextrose isomerase and to establish the flow pattern in the bed; and
   b. recovering a levulose bearing solution as the effluent.

* * * * *